United States Patent [19]
Schweichler et al.

[11] Patent Number: 5,146,485
[45] Date of Patent: Sep. 8, 1992

[54] X-RAY EXAMINATION APPARATUS

[75] Inventors: Gerd Schweichler, Dormitz; Michael Meyer, Roettenbach, both of Fed. Rep. of Germany

[73] Assignee: Siemens Aktiengesellschaft, Munich

[21] Appl. No.: 821,824

[22] Filed: Jan. 17, 1992

[30] Foreign Application Priority Data

Jan. 31, 1991 [DE] Fed. Rep. of Germany ....... 4102894

[51] Int. Cl.[5] ............................................. H05G 1/02
[52] U.S. Cl. .................................... 378/197; 378/196; 378/189
[58] Field of Search ............... 378/197, 189, 195, 196, 378/198, 39, 193

[56] References Cited

U.S. PATENT DOCUMENTS

| | | | |
|---|---|---|---|
| 4,541,293 | 9/1985 | Caugant et al. | 378/196 |
| 4,872,192 | 10/1989 | Hahn et al. | 378/197 |
| 4,894,855 | 1/1990 | Kresse | 378/196 |
| 5,014,292 | 5/1991 | Siczek et al. | 378/197 |

FOREIGN PATENT DOCUMENTS 2048022 11/1971 Fed. Rep. of Germany.
2608461 9/1977 Fed. Rep. of Germany.
3217478 6/1989 Fed. Rep. of Germany.

OTHER PUBLICATIONS

Brochure for "BV/FS-Universal-Deckenstativ" of Koch & Sterzel KG Röntgenwerk.
Brochure for "ARCOSKOP 100-3D" of Siemens AG.

Primary Examiner—Constantine Hannaher
Assistant Examiner—Don Wong
Attorney, Agent, or Firm—Hill, Van Santen, Steadman & Simpson

[57] ABSTRACT

An x-ray examination apparatus which enables free access to the patient in interventional radiology given a simple structural format has an x-ray radiator and an x-ray image intensifier at least one of which is adjustable on a spherical surface. To this end, at least one of these components, such as the x-ray image intensifier is suspended by a telescopically extendable circular arc section so as to be adjustable in a circumferential direction. The arc section is adjustable in ceiling rails extending perpendicular to the surface defined by the arc section. The suspended component is held in a holder so as to be pivotable around a transverse axis and the holder is longitudinally displaceable.

2 Claims, 3 Drawing Sheets

X-RAY EXAMINATION APPARATUS

BACKGROUND OF THE INVENTION

1. Field of the Invention

The invention is directed to an x-ray examination apparatus having an x-ray radiator and a radiation receiver that are mounted so as to be individually adjustable.

2. Description of the Prior Art

Radiologists who must intervene in the examination process prefer x-ray examination apparatus that allow good accessibility to the patient from all sides. In the known C-bend or U-bend apparatus for multidirectional transillumination, access to the patient is impeded at the bend side. It is known to adjustably seat the x-ray radiator and the radiation receiver with the assistance of carrier systems that are fashioned similar to an industrial robot and, controlled via control systems, can be pivoted motor-driven around the subject to be examined or treated. This known solution, however, requires great outlay for the hardware and for the software and for the safety monitoring.

SUMMARY OF THE INVENTION

It is an object of the invention to fashion an x-ray examination apparatus of the type described above such that a free accessibility to the patient is established with a simple structure.

This object is inventively achieved in that at least one of the x-ray radiator or radiation receiver is suspendedly adjustable in a circumferential direction at a circular arc section. The circular arc section is executed as a telescope, so that its length can be varied. The circular arc section is adjustable along rails perpendicular to the surface defined by the arc section. The component (components) suspended at the circular arc section is (are) pivotable at a holder around a transverse axis, this holder being adjustably suspended at the circular arc section. This suspended component is adjustable in its longitudinal direction with respect to the holder. In the x-ray examination apparatus of the invention, the circular arc section carrying the radiation receiver or the x-ray radiator can be fashioned relatively short in a known manner, as described in U.S. Pat. No. 4,541,293. Its length is increased only in the event that extreme, oblique transirradiations are undertaken. Free access to the patient is thus always guaranteed. The adjustment of the x-ray radiator or of the radiation receiver on a spherical surface is possible because the component suspended at the circular arc section is pivotable at a holder around a transverse axis that is adjustably suspended from the circular arc section, and this component is adjustable in its longitudinal direction relative to the holder.

DESCRIPTION OF THE PREFERRED EMBODIMENTS

Figure 1:
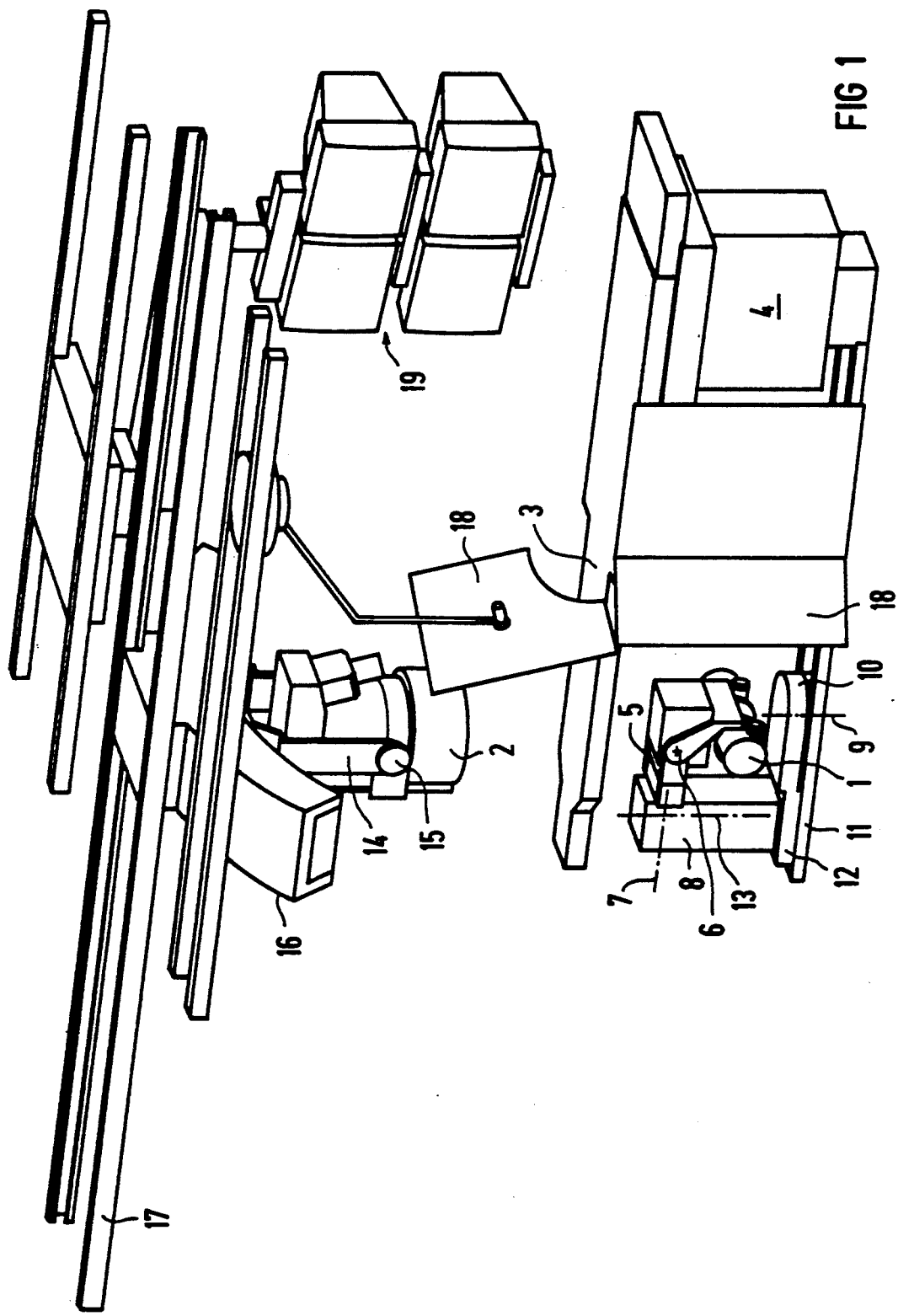
FIG. 1 is a perspective view of an x-ray examination apparatus constructed in accordance with the principles of the present invention.

FIG. 1 shows an x-ray examination apparatus which includes an x-ray radiator 1 and an x-ray image intensifier 2 as the radiation receiver. A patient support 3, that is adjustable on a pedestal 4, is disposed between the components 1 and 2. The x-ray radiator 1 is seated to be pivotable around a horizontal axis 6 at a holder 5. The holder 5 is connected to a telescoping stand 8 so as to be pivotable around a horizontal axis 7 extending perpendicularly vis-a-vis the axis 6. The telescoping stand 8 is connected to a holder 10 so as to be pivotable around a vertical axis 9. The holder 10 is displaceable in floor rails 11. An arm 12 carries the telescoping stand 8 so that the stand 8 is pivotable around a vertical axis 13. The x-ray radiator 1 is thus pivotable around the axes 6, 7, 9, and 13. Additionally, the x-ray radiator 1 is adjustable in height by shortening or lengthening the telescoping stand 8 in the vertical direction. The x-ray radiator 1 is thus adjustable on a spherical surface overall.

Figure 2:
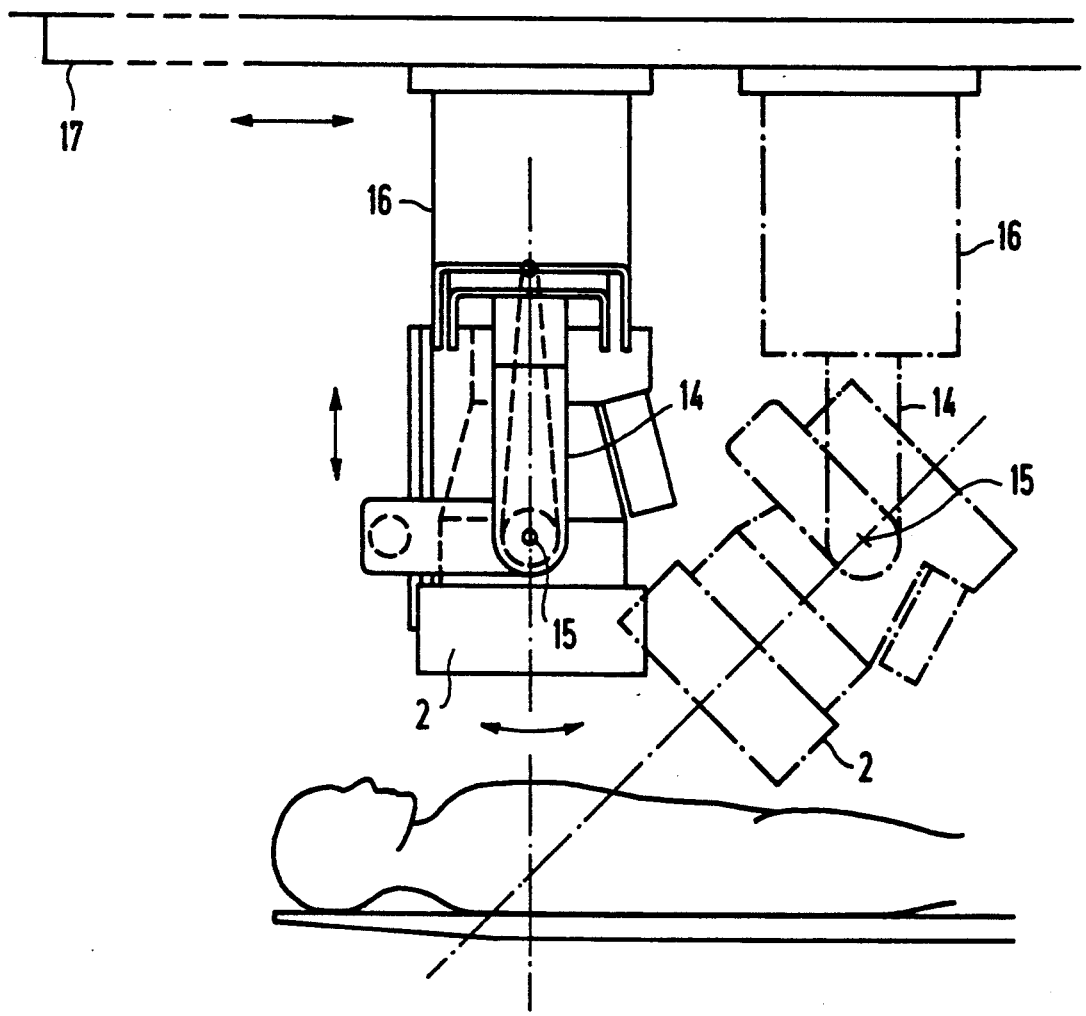
FIG. 2 is a side view of the apparatus of FIG. 1 showing the suspension of the x-ray image intensifier in various positions.

The x-ray image intensifier 2 is also adjustable on a spherical surface. To this end, it is suspended pivotably around a transverse axis 15 at a holder 14 and is also adjustable vis-a-vis the holder 14 in the longitudinal direction thereof. The holder 14 is suspended adjustable in a circumferential direction by a circular arc section 16. The circular arc section 16 is telescopically extendable and is adjustable in ceiling rails 17 running perpendicular to the surface defined by the arc section 16. The x-ray image intensifier 2 is shown in FIG. 2 in dot-dash lines in a position required for the oblique transirradiation of the patient, having been brought into this position by longitudinal displacement of the circular arc section 16 in the ceiling rails 17, by being pivoted around the transverse axis 15 and by longitudinal adjustment vis-a-vis the holder 14.

Figure 3:
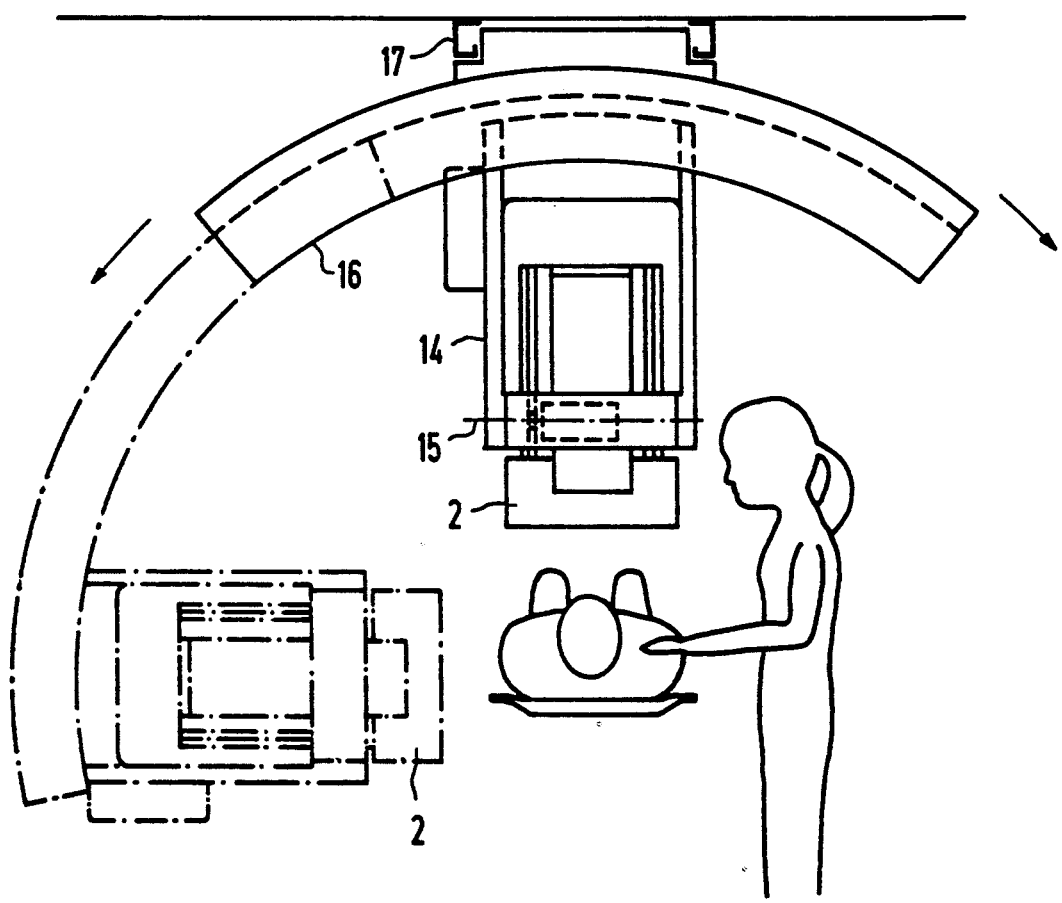
FIG. 3 is an end view of the apparatus of FIG. 1 showing the suspension of the x-ray image intensifier in various positions.

As shown in FIG. 3, the x-ray image intensifier 2 can be brought out of its position having a vertical longitudinal axis into a position having a horizontal longitudinal axis shown in dot-dash lines, by increasing the length of the circular arc section 16 telescopically.

A radiation shielding 18 for the examining person as well as a monitor 19 for viewing the x-ray images and for presentations of physiological quantities are also shown in FIG. 1.

Each of the components 1 and 2 is adjustable on a spherical surface in the x-ray examination apparatus of FIG. 1. This means that, in particular, the center point of the input luminescent screen of the x-ray image intensifier 2 as well as the focus of the x-ray radiator 1 respectively move on a spherical surface during the adjustment. To this end, the x-ray radiator 1—in the same way as the x-ray image intensifier 2—can also be adjustably seated at a correspondingly fashioned circular arc section that is adjustable in the floor rails 11.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray apparatus comprising:
   an x-ray radiator and an X-ray image intensifier disposed to receive x-rays from said x-ray radiator, said x-ray radiator and said x-ray image intensifier being adjustable components;

a circular arc section suspending one of said adjustable components, said circular arc section being telescopically adjustable in length and defining an imaginary surface;

rigidly mounted rails, extending perpendicularly to said surface, to which said circular arc section is mounted for adjustment along said rails; and a holder for said component suspended from said circular arc section, said holder being moveable with said component around the circular arc of said circular arc section, said holder being mounted to said circular arc section so as to be movable along a longitudinal axis of said holder and holding said component so that said component is pivotable around a transverse axis of said holder.

2. An x-ray examination apparatus as claimed in claim 1, wherein said component suspended from said circular arc section is said x-ray image intensifier.

* * * * *